US012766235B2

(12) United States Patent
Ruhland

(10) Patent No.: US 12,766,235 B2
(45) Date of Patent: Oct. 20, 2026

(54) FLOW RATE DEPENDENT BLOOD LEAK DETECTION SYSTEMS AND METHODS

(71) Applicant: GAMBRO LUNDIA AB, Lund (SE)

(72) Inventor: Daniel Ruhland, Roseville, MN (US)

(73) Assignee: Gambro Lundia AB, Lund (SE)

( * ) Notice: Subject to any disclaimer, the term of this patent is extended or adjusted under 35 U.S.C. 154(b) by 1086 days.

(21) Appl. No.: 17/283,746

(22) PCT Filed: Oct. 4, 2019

(86) PCT No.: PCT/EP2019/076877

§ 371 (c)(1),
(2) Date: Apr. 8, 2021

(87) PCT Pub. No.: WO2020/074377

PCT Pub. Date: Apr. 16, 2020

(65) Prior Publication Data

US 2021/0379267 A1 Dec. 9, 2021

Related U.S. Application Data

(60) Provisional application No. 62/743,906, filed on Oct. 10, 2018.

(51) Int. Cl.
*A61M 1/36* (2006.01)
*A61M 1/16* (2006.01)

(52) U.S. Cl.
CPC ........ *A61M 1/3656* (2014.02); *A61M 1/1623* (2014.02); *A61M 2205/18* (2013.01); *A61M 2205/3306* (2013.01); *A61M 2205/3334* (2013.01); *A61M 2230/207* (2013.01)

(58) Field of Classification Search
CPC ........ A61M 1/3656; A61M 2205/3306; A61M 2205/3334; A61M 1/1623; A61M 1/1609; A61M 1/1692; A61M 2205/18; A61M 2205/15; A61M 2205/3313; A61M 2205/331; A61M 2230/207
See application file for complete search history.

(56) References Cited

U.S. PATENT DOCUMENTS

| | | | | |
|---|---|---|---|---|
| 5,670,050 | A | 9/1997 | Brose | |
| 5,674,390 | A | 10/1997 | Matthews | |
| 5,762,805 | A | 6/1998 | Truitt | |
| 6,947,131 | B2 | 9/2005 | O'Mahony | |
| 7,264,730 | B2 * | 9/2007 | Connell .............. | A61M 1/1684 700/273 |

(Continued)

FOREIGN PATENT DOCUMENTS

| | | |
|---|---|---|
| WO | WO 97/11771 | 4/1997 |

OTHER PUBLICATIONS

PCT Search Report and Written Opinion for PCT/EP2019/076877 dated Jan. 7, 2020 (13 pages).

(Continued)

*Primary Examiner* — Kevin C Sirmons
*Assistant Examiner* — Leah J Swanson
(74) *Attorney, Agent, or Firm* — Mueting Raasch Group

(57) ABSTRACT

Systems and methods used to detect blood leaks (in, for example, extracorporeal blood treatment apparatus) by detecting the presence of blood in liquid above a selected threshold amount based on the flow rate of the liquid flowing through a passage (for example, a tube, etc.) are described.

23 Claims, 6 Drawing Sheets

(56) References Cited

U.S. PATENT DOCUMENTS

| | | | | |
|---|---|---|---|---|
| 9,585,992 | B2 * | 3/2017 | Bene | A61M 1/1609 |
| 2003/0210390 | A1 * | 11/2003 | O'Mahony | A61M 1/1692 356/218 |
| 2004/0129616 | A1 | 7/2004 | Mori | |
| 2013/0037485 | A1 | 2/2013 | Wilt | |
| 2017/0021088 | A1 | 1/2017 | Fulkerson | |
| 2019/0255241 | A1 * | 8/2019 | Gagel | A61M 1/1692 |

OTHER PUBLICATIONS

Swedish Search Report for Application No. 1950039-6 dated Dec. 16, 2019 (4 pages).

* cited by examiner

FLOW RATE DEPENDENT BLOOD LEAK DETECTION SYSTEMS AND METHODS

This application is a U.S. National Stage Application of International Application No. PCT/EP2019/076877 filed Oct. 4, 2019, which was published in English on Apr. 16, 2020 as International Publication No. WO 2020/074377 A1, which claims the benefit of 35 U.S.C. Section 119 of U.S. Provisional Application Ser. No. 62/743,906 filed Oct. 10, 2018.

BACKGROUND

The disclosure herein relates to detection of a blood leak into a liquid. More particularly, the disclosure relates to detection of a blood leak into a liquid flowing through a passage such as a tube, etc.

Extracorporeal blood treatment involves taking the blood from a patient, treating the blood outside the patient, and returning the treated blood to the patient. Extracorporeal blood treatment is typically used to extract undesirable matter or molecules from the patient's blood and/or to add beneficial matter or molecules to the blood. Extracorporeal blood treatment is used with patients incapable of effectively eliminating matter from their blood, for example, in the case of a patient who is suffering from temporary or permanent kidney failure. These and other patients may undergo extracorporeal blood treatment to add to or to eliminate unwanted matter from their blood, to maintain an acid-base balance, to eliminate excess body fluids (through, for example, ultrafiltration, etc.), etc.

In a variety of extracorporeal blood treatments, blood is passed through a first chamber of a filter, with the first chamber being separated from a second chamber of the filter by a semipermeable membrane. Liquid may be collected from the second chamber of the filter as a part of the treatments and the collected liquid may be referred to as "effluent." In, for example, dialysis treatments, a dialysate liquid is supplied to the second chamber and spent dialysate containing one or more constituents removed from blood passing through the first chamber is the effluent removed from the second chamber. In, for example, ultrafiltration treatments, liquid is removed from blood that contains an excessive amount of liquid, with the liquid (effluent) removed from the blood passing through the first chamber passing into the second chamber through the semipermeable membrane.

Blood leak detectors are used in extracorporeal blood treatment apparatus and methods to sense a rupture or other failure of a blood filter in which hemoglobin (and possibly other blood cells and larger solutes) pass from the first chamber into the second chamber. Such failures in blood filters should be detected to avoid loss of these blood cells and desirable solutes.

Many blood leak detectors operate by optically sensing hemoglobin in the fluid removed from the second chamber of a filter. A decrease in the amount of light passing through the liquid indicates the presence of hematocrit in the liquid and, therefore, a potential failure in the filter.

Known blood leak detectors and methods are, however typically set to identify the existence of a blood leak at a selected level of hemoglobin that is equivalent to a leak rate of, for example, 0.35 milliliters (mL) per minute. In alternative embodiments, the systems and methods set to identify the existence of a blood leak at a selected level of hemoglobin that is equivalent to even lower leak rates. Although such leak rates can be detected using known blood leak detectors for detecting blood in liquids moving at lower flow rates, they may not be capable of detecting unacceptable blood leak rates in liquids moving at higher flow rates.

SUMMARY

The present disclosure describes systems and methods which may be used to detect blood leaks (in, for example, extracorporeal blood treatment apparatus) by detecting the presence of blood in liquid above a selected threshold amount based on the flow rate of the liquid flowing through a passage (for example, a tube, etc.).

In known systems, the existence of a blood leak is identified when the detected concentration of blood in a liquid being monitored exceeds a constant threshold based on the transmission of light falling below a selected level. With a constant concentration alarm threshold, higher liquid flow rates result in higher blood loss as measured in volume of blood per minute. Regarding risk to the patient from blood leaking into a flowing liquid, the volume of blood loss versus time is the key factor, not necessarily the concentration of blood in the liquid. Some standards specify that a blood loss of less than 0.35 mL per minute is not harmful to the patient (for example IEC 60601-2-16).

Accordingly, optical blood leak detectors typically specify a threshold transmission for light passing through a liquid that is set to detect a fixed or constant blood concentration level corresponding to that allowed blood loss rate plus a margin of safety regardless of the flow rate of the liquid in which blood is being detected.

Such constant alarm thresholds may not, however, be sensitive enough to alarm when unacceptable blood leaks occur in liquids flowing at higher flow rates. Setting the allowable blood concentration level (based on light transmission) at a level capable of detecting unacceptable blood leaks at higher liquid flow rates would, however, typically result in an increase in the number of false alarms at lower flow rates.

In one or more embodiments of the present invention, the threshold amount of blood in a liquid being monitored that is used to identify the existence of a blood leak is different based on the flow rate of the liquid in which blood is being detected. For example, in one or more embodiments, the threshold amount may be set at a first value when the flow rate of the liquid is below a selected value, while the threshold amount is set at a second value when the flow rate of the liquid is above that selected value.

One potential advantage of using threshold amounts that change based on flow rate is acceptable detection at higher liquid flow rates while, at the same time, reducing the likelihood of false alarms at lower flow rates in which an unacceptable blood leak is identified but does not actually exist.

In a first aspect, one or more embodiments of the blood leak detection systems described herein may include: an optical source configured to emit light along an optical path; an optical detector configured to receive the light emitted by the optical source; a tube retainer configured to retain a tube such that the optical path passes through a liquid passing through a tube positioned in the tube retainer; and a controller operably connected to the optical detector, the controller configured to: receive a flow rate signal representative of a flow rate of liquid passing through a tube in the tube retainer; receive a detection signal from the optical detector, the detection signal representative of an amount of blood in liquid passing through the tube in the tube retainer; determine if the liquid passing through the tube in the tube retainer contains more than a threshold amount of blood based at least in part on the flow rate signal and the detection signal, wherein the threshold amount comprises a first value when the flow rate is below a selected flow rate and wherein the threshold amount comprises a second value when the flow rate is above the selected flow rate; and identify the existence of a blood leak when the liquid passing through the tube in the tube retainer contains more than the threshold amount of blood.

In one or more embodiments of the systems described herein, first value comprises a constant value when the flow rate is below the selected flow rate.

In one or more embodiments of the systems described herein, the second value increases as the flow rate increases. In one or more embodiments, the second value is directly proportional to the flow rate when the flow rate is above the selected flow rate.

In one or more embodiments of the systems described herein, the second value is constant.

In one or more embodiments of the systems described herein, the second value is greater than the first value.

In one or more embodiments of the systems described herein, the detection signal is representative of the amount of hematocrit in the liquid passing through the tube in the tube retainer.

In one or more embodiments of the systems described herein, the threshold amount of blood in the liquid passing through the tube in the retainer is equivalent to a blood leak rate of 0.35 milliliters per minute or less.

In one or more embodiments of the systems described herein, the controller is operably connected to an alarm and wherein the controller is configured to activate the alarm after identifying the existence of a blood leak.

In one or more embodiments of the systems described herein, the system comprises an extracorporeal blood treatment system that comprises: a filtration unit comprising a primary chamber and a secondary chamber separated by a semi-permeable membrane; a blood withdrawal line connected to an inlet of the primary chamber, and a blood return line connected to an outlet of the primary chamber, the blood withdrawal line and the blood return line being configured for connection to a patient cardiovascular system; a blood pump configured to control the flow of blood through the primary chamber; an effluent fluid line connected to an outlet of the secondary chamber, wherein the effluent line removes effluent liquid from the secondary chamber, and wherein the effluent line comprises the tube positioned in the tube retainer such that the controller is configured to determine if the effluent liquid removed from the secondary chamber contains more than the threshold amount of blood.

In a second aspect, one or more embodiments of the methods of identifying the existence of a blood leak in an extracorporeal treatment apparatus may include: emitting light from an optical source, the light traveling along an optical path passing through liquid flowing through a passage; detecting the light emitted by the optical source after the light has traveled through the liquid, wherein only a portion of the light passing through the liquid is transmitted to the detector when the liquid contains blood; identifying the existence of a blood leak into the liquid flowing through the passage by determining if the liquid flowing through the passage contains more than a threshold amount of blood based at least in part on a flow rate of the liquid and the portion of the light transmitted to the detector, wherein the threshold amount comprises a first value when the flow rate is below a selected flow rate and wherein the threshold amount comprises a second value when the flow rate is above the selected flow rate.

In one or more embodiments of the methods described herein, the first value comprises a constant value when the flow rate is below the selected flow rate.

In one or more embodiments of the methods described herein, the second value increases as the flow rate increases. In one or more embodiments, the second value is directly proportional to the flow rate when the flow rate is above the selected flow rate.

In one or more embodiments of the methods described herein, the second value is constant.

In one or more embodiments of the methods described herein, the second value is greater than the first value.

In one or more embodiments of the methods described herein, the portion of the light transmitted to the detector is representative of the amount of hematocrit in the liquid flowing through the passage. In one or more embodiments, the threshold amount of blood in the liquid flowing through the passage is equivalent to a blood leak rate of 0.35 milliliters per minute or less.

In one or more embodiments of the methods described herein, the method comprises activating an alarm after identifying the existence of a blood leak.

In one or more embodiments of the methods described herein, the method comprises an extracorporeal blood treatment method, and wherein the liquid flowing through the passage comprises effluent liquid containing one or more constituents removed from blood.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DESCRIPTION OF ILLUSTRATIVE EMBODIMENTS

Figure 1:
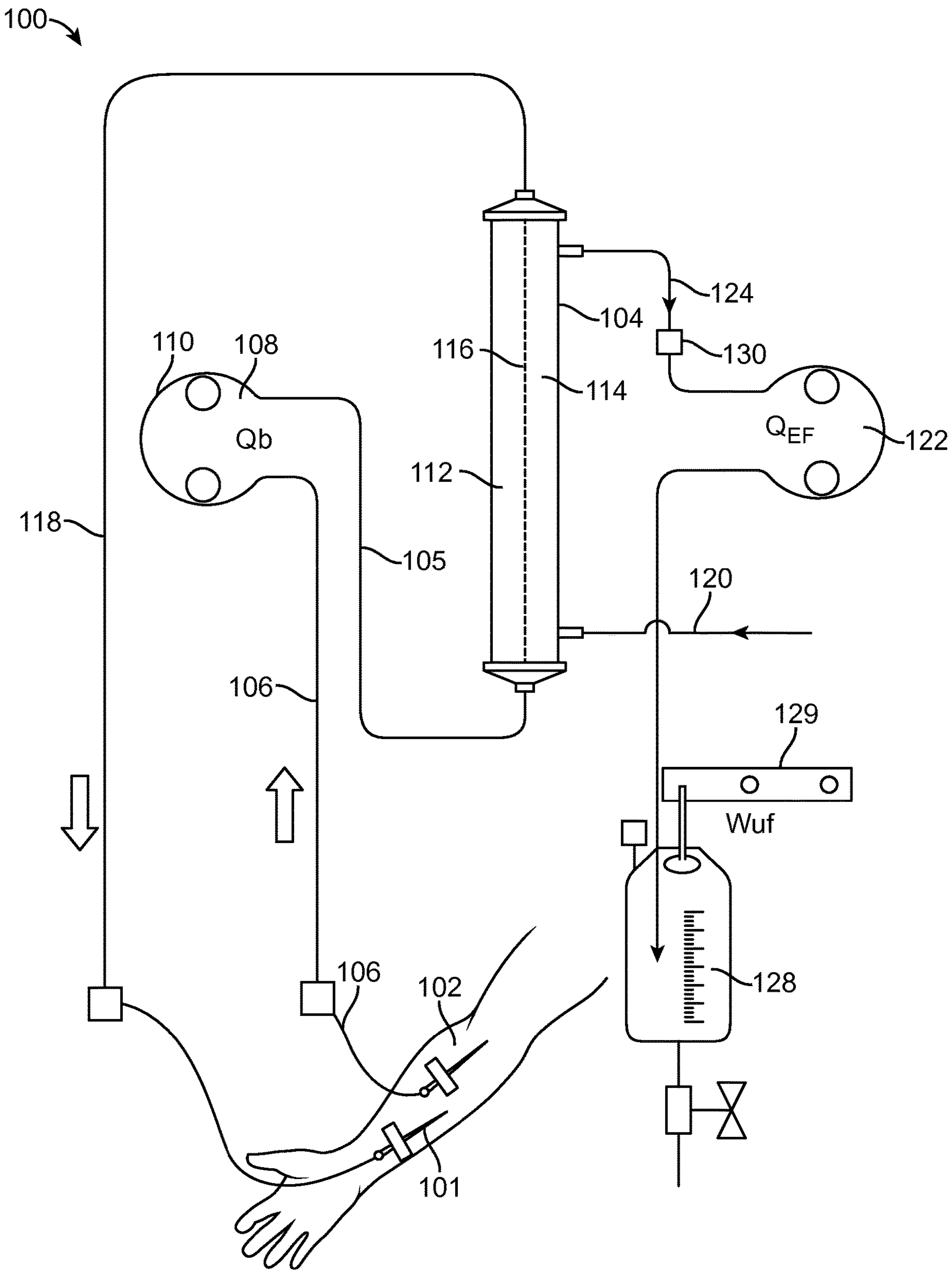
FIG. 1 is a schematic diagram of one illustrative embodiment of an extracorporeal blood treatment apparatus that may include and/or implement the blood leak detection system and methods described herein.

In the following description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (for example, still falling within) the scope of the disclosure described herein.

Exemplary systems, methods, and apparatus for use in identifying blood leaks in a liquid flowing through a tube or other passage shall be described with reference to FIGS. 1-7. The blood leak detection systems and methods described herein may be used in any extracorporeal blood treatment apparatus that would benefit therefrom. For example, extracorporeal blood treatment apparatus that may benefit from the blood leak detection systems and methods described herein may include ultrafiltration systems, dialysis systems, etc. The general term dialysis as used herein includes, for example, hemodialysis, hemofiltration, hemodiafiltration, and therapeutic plasma exchange (TPE), among other similar treatment procedures. In dialysis generally, blood is taken out of the body and exposed to a treatment device to separate substances therefrom and/or to add substances thereto and is then returned to the body. Specific examples of dialysis may include, but are not limited to, continuous renal replacement therapy (CRRT), extracorporeal membrane oxygenation (ECMO), hemoperfusion (HP), molecular adsorbent recirculating systems (MARS), cascade, etc. and the present disclosure is not limited to the specific extracorporeal blood treatment apparatus described herein.

FIG. 1 depicts the major components of one illustrative embodiment of an extracorporeal blood treatment apparatus 100 that extracts blood from a vein or artery in a patient 102, removes matter (for example, solutes, liquid, etc.) from the blood in a filter 104, and returns treated blood to the same or other vein or artery of the patient.

To withdraw blood, a withdrawal tube 106 is connected to a withdrawal cannula 102 inserted into a vein of the patient. The tube 106 leads the withdrawn blood to a blood pump 108 which acts on a tube loop 110 to move blood through the blood tubing. The rotational speed of the blood pump controls the withdrawal flow rate (Qb) of the blood through the withdrawal tube 106. From the pump 108, blood flows through the blood tube 105 to the filter 104.

The filter 104 may include a semipermeable membrane 116 that separates the filter 104 into a first chamber 112 and a second chamber 114. Blood removed from the patient is delivered to the first chamber 112 through blood tube 105 and returned to the patient through return line 118. The blood leaving the first chamber 112 of filter 104 is returned to the patient via an infusion cannula inserted into a peripheral vein of the patient 101.

In the depicted extracorporeal blood treatment apparatus 100, dialysate is delivered to the second chamber 114 of the filter 104 through supply line 120 and removed from the second chamber 114 through effluent line 124 using effluent pump 122. Effluent pump 122 may, in one or more embodiments, control the flow rate (Qef) through effluent line 124 by varying the rotational speed of the pump 122.

The effluent liquid removed from the second chamber 114 of the filter 104 may be collected in a reservoir before disposal or, in one or more alternative embodiments may be merely disposed of without collection. In the depicted illustrative embodiment, the effluent liquid is collected in container 128 which is operably connected to a weight scale 129 such that the weight (and therefore, volume) of effluent liquid removed from the second chamber 114 can be monitored.

As described herein, the extracorporeal blood treatment apparatus incorporating the blood leak detection systems and methods described herein rely on flow rate for the detection of blood leaks. Flow rate may be determined in such apparatus by a variety of techniques with, in one or more examples, two or more flow rate determination techniques may be used for redundancy and/or accuracy.

Effluent pump 122 used to remove spent dialysate or effluent from the second chamber 114 of filter 104 through effluent line 124 may be used to determine the flow rate of effluent or spent dialysate from the second chamber 114 of filter 104. Alternatively, the scale 129 used to weigh the collection container 128 used to collect the effluent may be used to determine the weight and, therefore, volume of the effluent removed from the second chamber 114 of filter 104 over time. As a result, the flow rate of effluent or spent dialysate from the second chamber 114 of filter 104 can be determined using the weight scale 129. In one or more embodiments in which both a pump and a weight scale are provided, the two sources of flow rate may be used in tandem for redundancy.

Although determination of flow rate is described herein as being accomplished using pumps and/or weight scales, flow rate through the effluent line 124 may, in one or more embodiments, be determined by direct measurement using flowmeters positioned and configured to measure flow rate of a liquid through a passage.

In the depicted illustrative embodiment of extracorporeal blood treatment apparatus 100, a blood leak detector 130 monitors the effluent line 124 for the presence of blood hemoglobin in the effluent liquid passing through effluent line 124. Blood hemoglobin in the effluent liquid indicates a rupture in the filter membrane or other failure of the filter 104 through which blood enters the effluent liquid. The detector 130 optically monitors the effluent for the presence of hemoglobin by sensing the absorption of light passing through the effluent line 124. Hemoglobins are large blood molecules that are too large to pass through the membrane of a properly functioning filter. If hemoglobin molecules do pass through the membrane or otherwise enter the second chamber 114 of filter 104, a failure is present in the filter. In one or more embodiments, the detector 130 transmits light one or more selected wavelengths through the effluent line 124 and detects the amount of light absorbed by the effluent liquid. The absorption of light in the infrared spectrum between 800 and 900 nm is, for example, strongly influenced by the presence of hemoglobin in the effluent.

As discussed in, for example, U.S. Pat. No. 6,947,131 B2 (see, for example, FIG. 2), the light absorption (in terms of molecular extinction coefficients) of different types of hemoglobin varies over wavelengths between 600 to 1000 nanometers (nm). The molecular extinction coefficient is a property of each hemoglobin type at each wavelength. For example, de-oxy hemoglobin (Hb) and oxy-hemoglobin ($O_2Hb$) in the effluent may be detected using light of selected wavelengths. Other types of hemoglobin, such as, for example, carboxy hemoglobin (CoHb) (which generally occurs in the blood of fire victims), and cyan-hemoglobin and meth-hemoglobin (MetHb) (which generally occur in the blood of poison victims) may also be detected. For purposes of a blood leak detector for an extracorporeal blood treatment apparatus, the optical properties of those extraordinary types of hemoglobin, i.e., carboxy-, cyan- and meth-hemoglobins, are typically not used to detect blood leaks.

The two most common hemoglobins (oxy and de-oxy) have identical or near light absorption characteristics, known as extinction coefficients, at 820 nm. The light absorption of oxy-hemoglobin ($O_2Hb$) and de-oxy hemoglobin (Hb) is substantially the same for wavelengths from about 800 nm to 930 nm, and from about 250 nm to 600 nm (not shown). In one or more embodiments, a blood leak detector system and method as described herein may use light at or near 820 nm, for example between 800 to 930 nm, to be generally equally responsive to oxy- and de-oxy hemoglobins flowing in the effluent line (or other passage through which liquid flows and in which blood is to be detected).

The blood leak detector exploits the fact that the extinction coefficients of oxy and de-oxy hemoglobin are substantially equal in the range of wavelengths from about 800 nm to 930 nm. By emitting and detecting light in this range, a blood leak detector may be relatively insensitive to blood oxygenation because the light adsorption characteristics are substantially the same for oxy and de-oxy hemoglobin.

In one or more embodiments, the blood leak detectors used in blood leak detection systems described herein, may use a light source, for example, light emitting diode (LED), and a matched light detector, for example, photodiode, that have narrow spectral emission and detectivity curves. The spectral optical peak of these devices is preferably 800 nm to 930 nm (nanometers) in the infrared spectrum. These wavelengths of light are equally absorbed by oxy- and de-oxy hemoglobin. The effects of ambient light on the blood leak detector 130 may be limited through use of shielding and reliance on a narrow spectral zone. In one or more embodiments, the blood leak detector may also include a modulated drive for the LED (light emitting diode) and a synchronous demodulator that are arranged to further reduce the responsiveness of the detector to ambient light interference.

Figure 2:
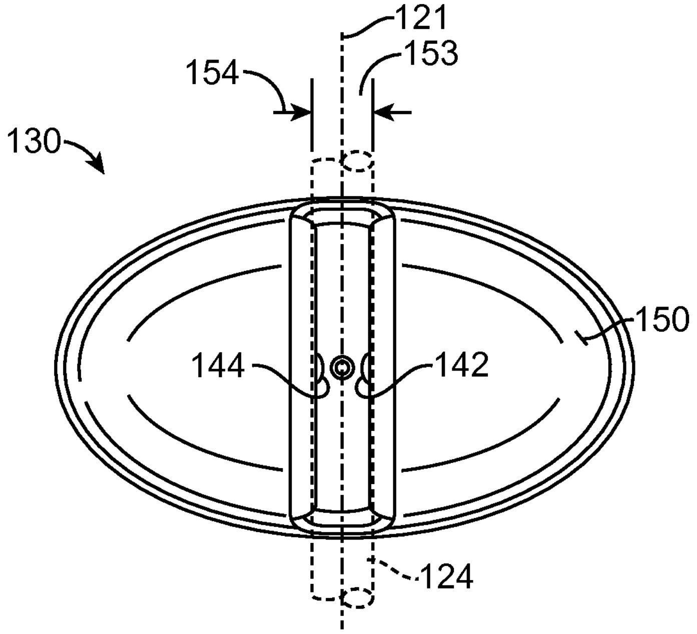
FIG. 2 depicts one illustrative embodiment of a tube retainer and optical components of a blood leak detection system as described herein.

FIG. 2 depicts one illustrative embodiment of a blood leak detector 130 that may be used in one or more blood treatment apparatus as described herein. The blood leak detector 130 may include a housing 150 formed of a material, for example, opaque plastic, that blocks ambient light, particularly at the wavelengths of the light being used to detect blood.

The housing 150 includes a tube retainer or slot 153 in which tubing 124 may be received. The retainer or slot 153 defines a flow axis 121 through which liquid moves through the slot 153. The slot 153 may, in one or more embodiments, be smaller than the width of the tubing 124 to securely hold the tube in the slot 153, although clamps covers, etc. may be used in place of or in addition to friction to retain the tubing 124 within slot 153.

An optical source 142 and an optical detector 144 are, in the illustrative embodiment, located within slot 153. The optical source 142 is configured to emit light along an optical path that includes the optical detector 144. The optical detector is configured to receive the light emitted by the optical source. The tube retainer/slot 153 is configured to retain a tube, such as, for example, effluent to 124, such that the optical path between the optical source 142 and the optical detector 144 passes through a liquid (for example, effluent) passing through the tube 124 positioned in the tube retainer/slot 153.

The housing 150 and associated optical source 142 and optical detector 144 of blood leak detector 130 depict only one example of an arrangement of components that may be used to detect blood in a liquid as described herein. In particular, the depicted assembly may be described as defining a single optical path through a tube or other passage carrying a liquid that may contain blood which needs to be detected.

Figure 3:
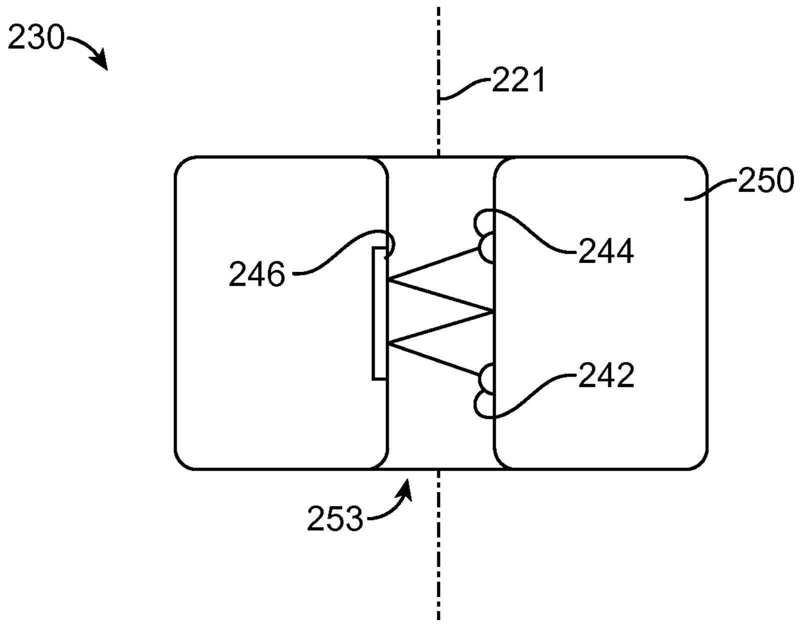
FIG. 3 depicts another illustrative embodiment of a tube retainer and optical components of a blood leak detection system as described herein

An alternative embodiment of a blood leak detector 230 is depicted in connection with FIG. 3. FIG. 3 includes a housing 250 defining a slot 253 configured to receive and retain a tube or other liquid passageway. Liquid flowing through the slot 253 moves along the flow axis 221.

In the depicted illustrative embodiment of a blood leak detector 230, the optical source 242 and optical detector 244 are located on the same side of the passageway 253. A reflector 246 may be positioned on the opposite side of the slot 253 such that an optical path may be created across the slot 253 that includes multiple segments. In other words, light emitted by optical source 242 may pass through a tube or other conduit two or more times before reaching the optical detector 244. In one or more embodiments, such a multi-pass system may improve the ability of the optical detector to detect blood in a liquid flowing through a tube or other conduit located in slot 253.

In one or more alternative embodiments, a separate reflector 246 may or may not be required where, for example, the tubing or conduit used to move liquid past the optical source 242 and optical detector 244 and/or, the liquid itself provides sufficient reflectivity to provide a multi-pass optical detection system.

As discussed herein, the blood leak detection systems and methods rely on flow rate in addition to the optical detection of blood in a liquid to provide acceptable detection at higher liquid flow rates while, at the same time, reducing the likelihood of false alarms at lower flow rates in a which an unacceptable blood leak is identified but does not actually exist.

Figure 4:
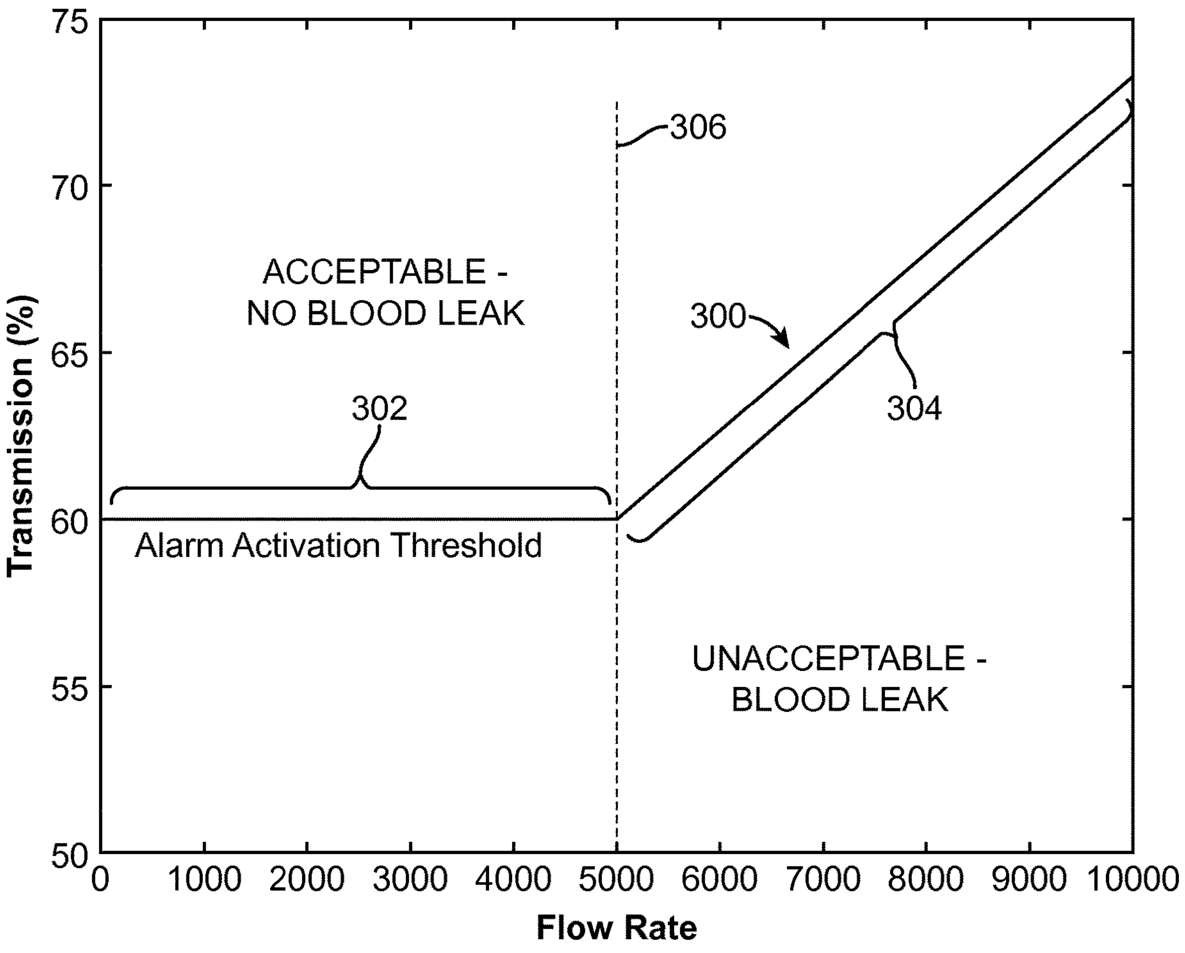
FIG. 4 is a graphical illustration of one illustrative embodiment of a method of blood leak detection as described herein.

FIG. 4 is a graphical representation of one illustrative embodiment of the thresholds used to identify the existence of a blood leak based on the percent of light transmitted through a flowing liquid as a function of the flow rate. It should be understood that the specific values depicted in this graph are exemplary only and that other values for transmission percentage and flow rate may apply in other systems.

In one or more embodiments, the blood leak detection systems and methods described herein may identify the existence of a blood leak into liquid flowing through a passage by determining if the liquid flowing through the passage contains more than a threshold amount of blood based, at least in part, on a flow rate of the liquid and the portion or percentage of the light transmitted to the detector.

In one or more embodiments, the threshold amount of blood in a liquid being monitored that is used to identify the existence of a blood leak is different based on the flow rate of the liquid in which blood is being detected. For example, in one or more embodiments, the threshold amount may be set at a first value when the flow rate of the liquid is below a selected flow rate value, while the threshold amount is set at a second value when the flow rate of the liquid is above that selected flow rate value.

As discussed in, for example, U.S. Pat. No. 6,947,131 B2, relationships between the percent light transmission and hemoglobin concentration are known. from a blood leak detector. Hematocrit (Hct) is a term commonly used to describe the concentration of red blood cells (RBC) or hemoglobin in blood or in other liquids such as, effluent or filtrate removed from a blood filter of an extracorporeal blood treatment apparatus. Hematocrit (Hct) is the percent of whole blood that is comprised of red blood cells (RBC). The hematocrit is a relative measure of RBC volume. As the blood concentration (Hct) in a liquid increases, the optical transmission (% T) decreases. Due to the non-linearity of Beer's Law, the sensitivity to hemoglobin is high at low concentrations. Due to high sensitivity, and optical blood leak detector may be highly responsive to the presence of even small amounts of hemoglobin in a liquid. A sensor may be calibrated and normalized as discussed in, for example, U.S. Pat. No. 6,947,131 B2. In one or more embodiments, sensors may be capable of detecting a concentration of less than 0.5% Hct in a liquid.

With reference to FIG. 4, one illustrative embodiment of an alarm activation threshold as a function of transmission percentage and flow rate is depicted. In the depicted illustrative embodiment, flow rate may vary from 0 to 10,000 mL per hour along the X or horizontal axis, while only a portion of a transmission percentage from 50% to 75% is depicted along the Y or vertical axis. These ranges are exemplary only and the systems and methods described herein may operate within any selected set of ranges as required for desired operation.

Within those ranges, one illustrative embodiment of an alarm activation threshold curve 300 is depicted. The threshold curve 300 includes a first portion 302 and a second portion 304. The first portion 302 and second portion 304 are located on opposite sides of a selected flow rate 306 which, in the illustrative embodiment depicted in FIG. 4, is set at a flow rate of 5000 mL per hour.

With respect to the first portion 302 of the threshold curve 300, the threshold amount or percent transmission of light detected is a constant value of approximately 60%. When a blood leak detector as described herein detects a percent transmission of light through a liquid flowing through a tube of the blood leak detector that is above the threshold amount (for example, 65% or more transmission), the system does not identify the existence of a blood leak. Where, however, the transmission percentage falls below the activation threshold amount (for example, 55% or less transmission) and the flow rate is below the selected flow rate value of 5000 mL per hour, the blood leak detector system identifies the acceptance of a blood leak and can take appropriate actions (for example, activating an alarm, stopping a blood pump, etc.).

In the depicted illustrative embodiment, the first value for the threshold amount as embodied by portion 302 of curve 300 is a constant value when the flow rate is below the selected flow rate. In one or more alternative embodiments, however, the first value for the threshold amount may change based on flow rate. For example, the first value for the threshold amount at flow rates below the selected flow rate may increase with flow rate increases in a manner similar to the second portion 304 of the threshold curve 300.

With respect to the second portion 304 of the threshold curve 300, the threshold amount or percent transmission of light detected varies. In the depicted illustrative embodiment, the threshold amount or percent transmission of light detected increases as the flow rate increases. In the depicted illustrative embodiment, that relationship is linear and directly related to the flow rate.

In one or more alternative embodiments, however, the second value of the threshold amount for flow rates above the selected flow rate may be constant (but different than the first value) or may vary with flow rate based on any other selected relationship, for example, exponentially, logarithmically, or according to any other selected function.

Figure 5:
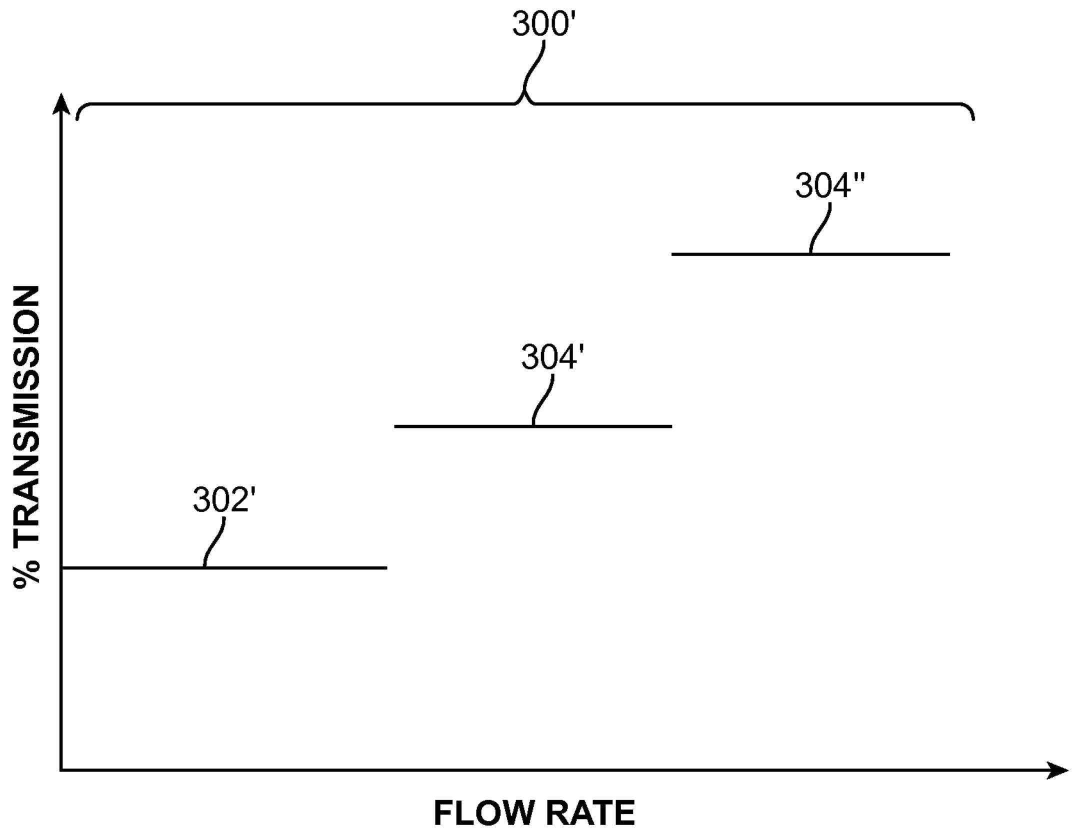
FIG. 5 is a graphical illustration of another illustrative embodiment of a method of blood leak detection as described herein.

In still other alternative embodiments, the threshold amounts may vary in a stepwise manner based on flow rate. One example of a curve 300' in which the threshold amounts vary in a stepwise manner based on flow rate is depicted in FIG. 5. The threshold curve 300' depicted in FIG. 5 includes a first portion 302', second portion 304', and third portion 304". The transmission percentage rises with flow rate in the second and third portions 304' and 304" as compared to the transmission percentage for the first portion 302'. The selected number of steps in the threshold curve 300' is exemplary only and embodiments of blood leak detector systems and methods described herein may include only a single step or two or more steps. Further, although depicted as constant within each portion, the threshold curve 300' may vary directly with flow rate within each portion (as seen in, for example, portion 304 of threshold curve 300 in FIG. 4) or may vary exponentially, logarithmically, or according to any other selected function within one or more selected portions.

In one or more embodiments, the systems and methods described herein may include a delay period before identifying the existence of a blood leak to avoid a false alarm in the case of, for example, a temporary event such as, for example, an air bubble that may temporarily decrease light transmission (due to, for example, refraction, etc.). In such systems and methods, the delay period over which the identification of a blood leak may be "held" even though the light transmission is below the threshold amount for the flow rate may, for example, be a period of 5 seconds or more, 10 seconds or more, 20 seconds or more, 30 seconds or more, etc. If, after the delay period the light transmission remains below the threshold amount for the flow rate, then the system and method would identify the existence of a blood leak.

Figure 6:
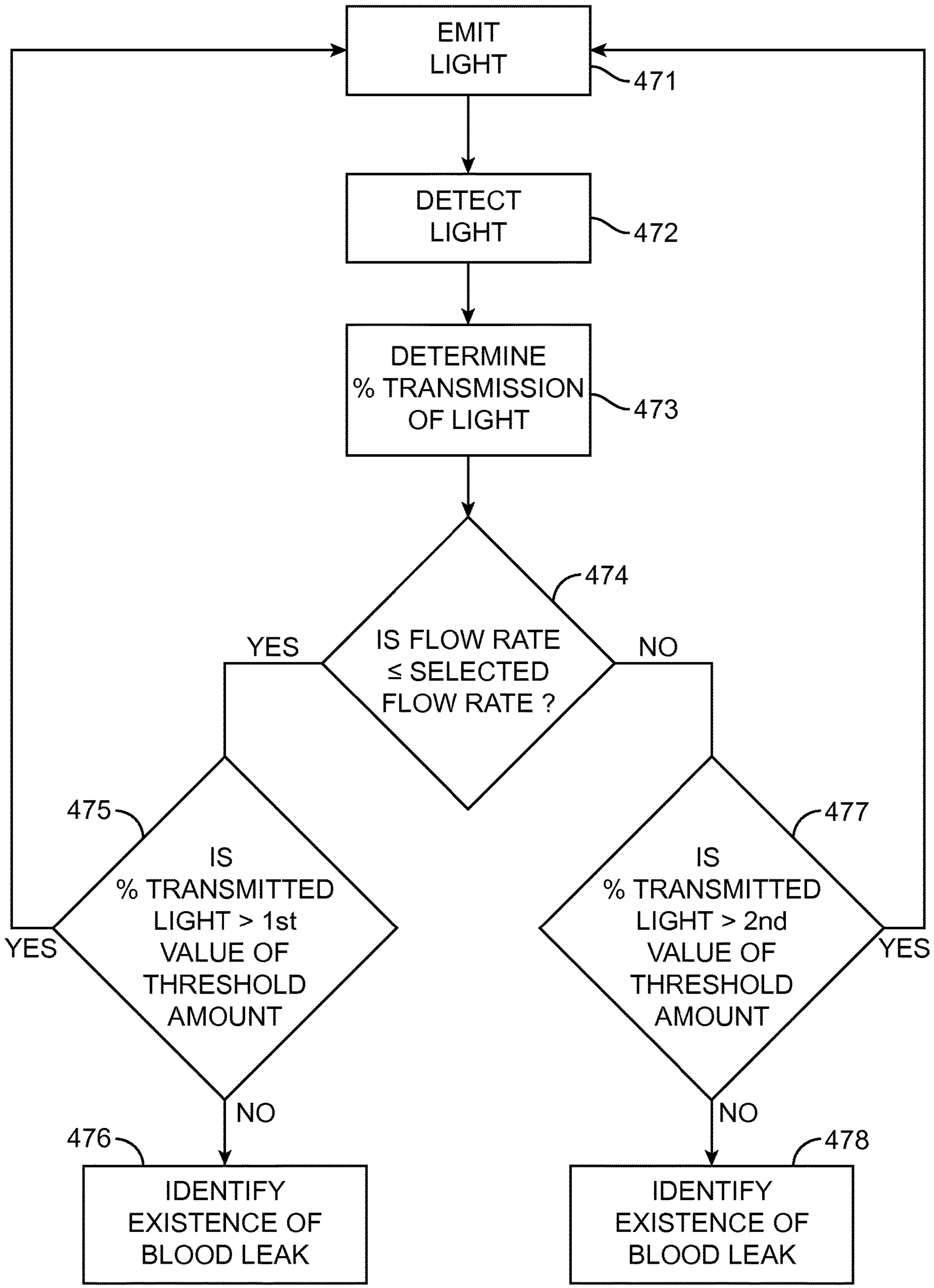
FIG. 6 is a block diagram illustrating one illustrative embodiment of a blood leak detection method as described herein.

FIG. 6 is a block diagram depicting one illustrative embodiment of a blood leak detection method as described herein. In the depicted illustrative embodiment, the method includes emitting light from an optical source 471. In one or more embodiments, the light travels along an optical path passing through liquid (for example, effluent, filtrate, etc.) flowing through a passage (for example, tubing, conduit, etc.).

The method further includes detecting the light emitted by the optical source 472. In one or more embodiments, the light is detected after it has traveled through the liquid, with only a portion of the light passing through the liquid being transmitted to the detector when the liquid contains blood.

The method may include, in one or more embodiments, determining the percent transmission of light through the liquid 473. As described herein, a decreasing percentage of light transmission correlates with an increasing amount of blood in the liquid.

The method also includes determining the flow rate of the liquid passing through the passage. In particular, the method involves determining if the flow rate is above or below a selected flow rate 474.

If the flow rate of the liquid is below the selected flow rate 474, a determination is made as to whether the liquid flowing through the passage contains more than a threshold amount of blood 475. This determination may, in one or more embodiments, correlate to the first portion 302 of the threshold curve 300 in FIG. 4 and is based on the percent of light transmitted through the liquid as described herein. If the percent of light transmitted is greater than the threshold amount, the method continues to monitor the system for a blood leak by emitting and detecting light as described herein. If, however, the percent of light transmitted is less than the threshold amount, the method includes identifying the existence of a blood leak 476 (after, in one or more embodiments, waiting to see if the light transmission remains below the threshold amount for a selected delay period as discussed herein). As discussed herein, identification of a blood leak may involve further action such as, for example, notifying a user or other individual through an alarm.

If the flow rate of liquid is above the selected flow rate 474, a determination is made as to whether the liquid flowing through the passage contains more than a threshold amount of blood 477. This determination may, in one or more embodiments, correlate to the second portion 304 of the threshold curve 300 in FIG. 4 and is based on the percent of light transmitted through the liquid as described herein. If the percent of light transmitted is greater than the threshold amount, the method continues to monitor the system for a blood leak by emitting and detecting light as described herein. If, however, the percent of light transmitted is less than the threshold amount, the method includes identifying the existence of a blood leak 478. As discussed herein, identification of a blood leak may involve further action such as, for example, notifying user or other individual through an alarm.

In those instances where the compared values of flow rate is equal to the selected flow rate or the light transmission percentage is equal to the threshold amount, the methods and systems described herein may proceed with either option available. For example, if the flow rate is equal to the selected flow rate than either of the first value or second value of the threshold amounts may be used to identify the existence of a blood leak. Similarly, if the light transmission percentage is equal to the threshold amount for a given flow rate, one or more embodiments of the system/method may be configured to identify the existence of a blood leak while in other embodiments, the system/method may be configured to not identify existence of a blood leak.

Figure 7:
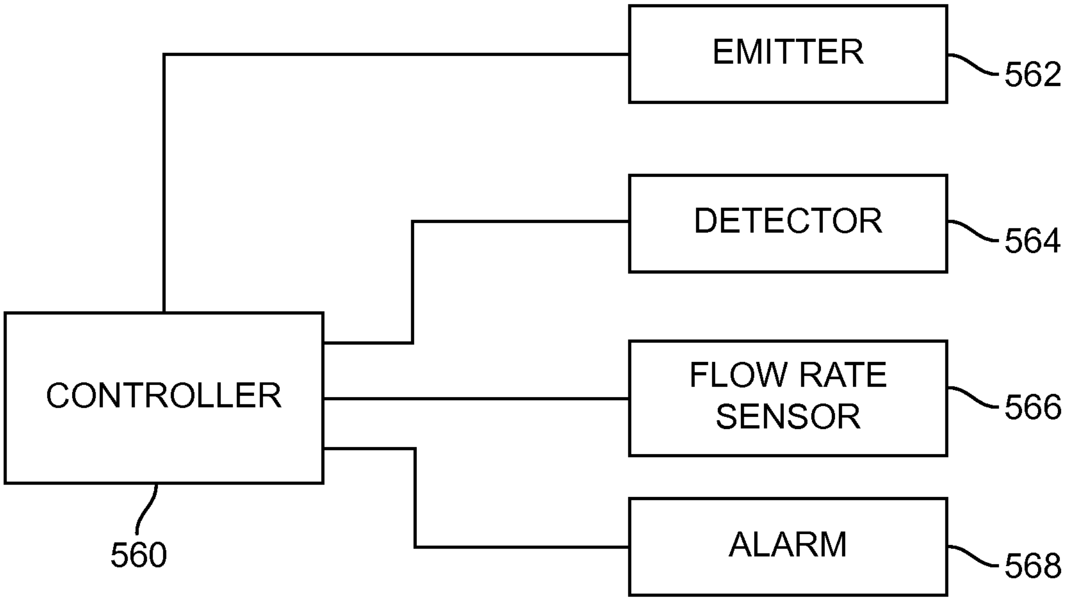
FIG. 7 is a block diagram of components that may be included in one illustrative embodiment of a blood leak detection system as described herein.

One illustrative embodiment of a blood leak detection system as described herein is schematically depicted in the block diagram of FIG. 7. In particular, FIG. 7 depicts a controller 560 operably connected to an optical source/emitter 562 and an optical detector 564. The controller 560 is also operably connected to a flow rate sensor 566 and an alarm 568.

As described herein, the flow rate sensor 566 may take a variety of different forms. For example, in one or more embodiments, the flow rate sensor 566 may be in the form of a pump which is monitored and/or controlled to provide a selected flow rate, a weight scale used to weigh liquid collected after passing through the blood leak detector such that the volumetric flow rate through the blood leak detector can be determined, a dedicated flow rate sensor configured to detect liquid flowing through a tube or other conduit, etc.

Similarly, the alarm 568 operably connected to the controller 560 may also take a variety of forms. For example, in one or more embodiments, the alarm 568 may provide one or more visual, audible, and/or tactile indications to a user and/or patient when a blood leak has been detected. As such, the alarms used in one or more embodiments of blood leak detector systems described herein may be implemented through the use of computer displays, lights, speakers, buzzers, etc.

The controller 560 used in one or more embodiments of blood leak detection systems and methods described herein may be any hardware/software architecture configured to provide the desired functionality. For example, the controller may include circuitry for controlling and/or sampling the optical source, optical detector, flow rate sensor, processing apparatus and associated software for processing data (for example, signals representative of light detected or flow rates to implement the monitoring and/or detection algorithms described herein), output circuitry to generate control signals for use in controlling the optical source and/or detector, for controlling one or more alarms, etc.

Such processing apparatus may be, for example, any fixed or mobile computer system (for example, a personal computer or mini-computer associated with, for example, a fluid treatment or processing system, such as a dialysis system). The exact configuration of the computing apparatus is not limiting and essentially any device capable of providing suitable computing capabilities and control capabilities (for example, control of the optical source, optical detector, flow rate sensing, etc.) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (for example, volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing analysis of measurement data, generation of control signals, etc.

Software or programs used to implement the functionality described herein may be provided using any programmable language, for example, a high level procedural and/or object orientated programming language that is suitable for communicating with a processing apparatus. Any such programs may, for example, be stored on any suitable device, for example, a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a specific and predefined manner to perform functions described herein.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An extracorporeal blood treatment system comprising:

a filtration unit comprising a primary chamber and a secondary chamber separated by a semi-permeable membrane;

a blood withdrawal line connected to an inlet of the primary chamber and a blood return line connected to an outlet of the primary chamber, the blood withdrawal line and the blood return line being configured for connection to a patient cardiovascular system;

a blood pump configured to control the flow of blood through the primary chamber;

an effluent line connected to an outlet of the secondary chamber, wherein the effluent line is configured to remove effluent liquid from the secondary chamber;

an optical source configured to emit light along an optical path;

an optical detector configured to receive the light emitted by the optical source;

a tube retainer configured to retain a tube such that the optical path passes through a liquid passing through the tube positioned in the tube retainer, wherein the effluent line comprises the tube positioned in the tube retainer; and a controller operably connected to the optical detector, the controller configured to:

receive a flow rate signal representative of a flow rate of liquid passing through the tube in the tube retainer;

receive a detection signal from the optical detector, the detection signal being indicative of a percent transmission of the light emitted by the optical source along the optical path that is received by the optical detector, the detection signal representative of an amount of blood in liquid passing through the tube in the tube retainer;

when the flow rate signal indicates that the flow rate is below a selected flow rate, determine existence of a blood leak when the percent transmission of the light emitted by the optical source along the optical path that is received by the optical detector as indicated by the detection signal from the optical detector is below a first value; and when the flow rate signal indicates that the flow rate is above the selected flow rate after the flow rate signal indicates that the flow rate is below the selected flow rate, determine existence of a blood leak when the percent transmission of the light emitted by the optical source along the optical path that is received by the optical detector as indicated by the detection signal from the optical detector is below a second value, wherein the second value is greater than the first value;

wherein the first value comprises a constant value when the flow rate is below the elected flow rate.

2. A system according to claim 1, wherein the second value increases as the flow rate increases.

3. A system according to claim 1, wherein the second value is directly proportional to the flow rate when the flow rate is above the selected flow rate.

4. A system according to claim 1, wherein the second value is constant.

5. A system according to claim 4, wherein the selected flow rate comprises a first selected flow rate and wherein, when the flow rate signal indicates that the flow rate is above a second selected flow rate, determine existence of a blood leak when the percent transmission of the light emitted by the optical source along the optical path that is received by the optical detector as indicated by the detection signal from the optical detector is below a third value, wherein the second selected flow rate is greater than the first selected flow rate and the third value is greater than the second value.

6. A system according to claim 5, wherein the third value is constant.

7. A system according to claim 1, wherein the detection signal is representative of an amount of hematocrit in the liquid passing through the tube in the tube retainer.

8. A system according to claim 1, wherein the first value and the second value are equivalent to a blood leak rate of 0.35 milliliters per minute or less.

9. A system according to claim 1, wherein the controller is operably connected to an alarm and wherein the controller is configured to activate the alarm after identifying the existence of a blood leak.

10. A system according to claim 1, wherein the optical source and optical detector are on a same side of the tube retainer.

11. A system according to claim 1, wherein when the flow rate signal indicates that the flow rate is below the selected flow rate, the controller is configured to determine the existence of a blood leak only when the percent transmission of the light emitted by the optical source along the optical path that is received by the optical detector as indicated by the detection signal from the optical detector is below the first value for a selected delay period.

12. A system according to claim 1, wherein when the flow rate signal indicates that the flow rate is above the selected flow rate, the controller is configured to determine existence of a blood leak only when the percent transmission of the light emitted by the optical source along the optical path that is received by the optical detector as indicated by the detection signal from the optical detector is below the second value for at least a selected delay period.

13. A method of detecting an existence of a blood leak in an extracorporeal treatment apparatus, the method comprising:

emitting light from an optical source, the light traveling along an optical path passing through liquid flowing through a passage;

detecting the light emitted by the optical source after the light has traveled through the liquid, wherein only a portion of the light passing through the liquid is transmitted to a detector when the liquid contains blood;

first identifying existence of a blood leak into the liquid flowing through the passage when the portion of the light transmitted to the detector through the liquid is below a first value when the flow rate is below a selected flow rate; and then identifying existence of a blood leak into the liquid flowing through the passage when the portion of the light transmitted to the detector through the liquid is below a second value when the flow rate is above the selected flow rate after the first identifying, wherein the second value is greater than the first value:

wherein the first value comprises a constant value when the flow rate is below the selected flow rate.

14. A method according to claim 13, wherein the second value increases as the flow rate increases.

15. A method according to claim 13, wherein the second value is directly proportional to the flow rate when the flow rate is above the selected flow rate.

16. A method according to claim 13, wherein the second value is constant.

17. A method according to claim 16, wherein the selected flow rate comprises a first selected flow rate and wherein, when the flow rate is above a second selected flow rate, identifying the existence of a blood leak when the portion of light transmitted to the detector through the liquid is below a third value, wherein the second selected flow rate is greater than the first selected flow rate and the third value is greater than the second value.

18. A method according to claim 17, wherein the third value is constant.

19. A method according to claim 13, wherein the portion of the light transmitted to the detector is representative of an amount of hematocrit in the liquid flowing through the passage.

20. A method according to claim 19, wherein the first value and the second value are equivalent to a blood leak rate of 0.35 milliliters per minute or less.

21. A method according to claim 13, wherein the method comprises activating an alarm after identifying the existence of a blood leak.

22. A method according to claim 13, wherein the method comprises an extracorporeal blood treatment method, and wherein the liquid flowing through the passage comprises effluent liquid containing one or more constituents removed from blood.

23. A method according to claim 13, wherein the detecting light emitted by the optical source is done with an optical detector, and wherein the optical source and optical detector are on a same side of the passage.

* * * * *